(12) United States Patent
Matoba

(10) Patent No.: US 9,001,966 B2
(45) Date of Patent: *Apr. 7, 2015

(54) TRANSMISSION X-RAY ANALYZER

(71) Applicant: Hitachi High-Tech Science Corporation, Minato-ku, Tokyo (JP)

(72) Inventor: Yoshiki Matoba, Chiba (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 146 days.

This patent is subject to a terminal disclaimer.

(21) Appl. No.: 13/769,704

(22) Filed: Feb. 18, 2013

(65) Prior Publication Data

US 2013/0216024 A1 Aug. 22, 2013

(30) Foreign Application Priority Data

Feb. 21, 2012 (JP) ................................ 2012-034792

(51) Int. Cl.
  *G01N 23/083* (2006.01)
  *H05G 1/02* (2006.01)
  *G21K 5/10* (2006.01)
  *G01N 21/86* (2006.01)
  *H01J 37/20* (2006.01)
  *G01N 23/04* (2006.01)

(52) U.S. Cl.
  CPC ....................................... *G01N 23/04* (2013.01)

(58) Field of Classification Search
  USPC ............. 378/51, 58, 62, 91, 98.8, 98.12, 189, 378/204, 208, 210; 250/306, 440.11, 250/442.11, 589, 328, 370.01, 370.08, 250/370.09, 370.1, 370.11, 370.14, 371, 250/559.01, 559.03, 559.07, 559.4, 559.41, 250/559.46, 453.11, 491.1, 526
  See application file for complete search history.

(56) References Cited

U.S. PATENT DOCUMENTS 2,570,288 A * 10/1951 Todd .............................. 209/587
3,317,736 A * 5/1967 Herrick et al. ................ 356/430
6,324,249 B1 * 11/2001 Fazzio ............................ 378/22

* cited by examiner

*Primary Examiner* — Anastasia Midkiff
(74) *Attorney, Agent, or Firm* — Brinks Gilson & Lione

(57) ABSTRACT

A transmission X-ray analyzer (1) for detecting a transmission X-ray image of a sample (100) that is continuous in a band shape includes: a TDI sensor (14); an X-ray source (12) arranged opposed to a TDI sensor; a pair of support rollers (31, 32) arranged away from the TDI sensor between the TDI sensor and the X-ray source, the pair of support rollers being configured to transport the sample to a detection position of the TDI sensor while keeping a constant interval between the TDI sensor and the sample; and a pair of outside rollers (51, 52) arranged respectively on an outer side of the pair of support rollers in a transportation direction (L). One of the pair of support rollers and one of the pair of outside rollers are arranged at different positions as to apply a tension to the sample between the pair of support rollers.

2 Claims, 3 Drawing Sheets

(a)

(a)

(b)

TRANSMISSION X-RAY ANALYZER

RELATED APPLICATIONS

This application claims priority under 35 U.S.C. §119 to Japanese Patent Application No. 2012-034792 filed on Feb. 21, 2012, the entire content of which is hereby incorporated by reference.

BACKGROUND OF THE INVENTION

1. Field of the Invention

The present invention relates to a transmission X-ray analyzer, which is capable of measuring a transmission X-ray output from a sample through use of a time delay and integration (TDI) sensor.

2. Description of the Related Art

Conventionally, a foreign matter in a sample and density unevenness of elements have been detected by X-ray transmission imaging. As a method of the X-ray transmission imaging, there is known a method of converting a transmission X-ray output from a sample into fluorescent light through a fluorescent screen or the like, and detecting the fluorescent light through use of image pickup devices (charge coupled devices (CCDs)). As a detection method using CCDs, there is a method of scanning a sample to obtain linear images successively through use of a line sensor having a plurality of image pickup devices arranged in one direction, thereby obtaining a two-dimensional image of the sample.

By the way, when the movement speed of a sample in a transportation direction increases, the time period of accumulation of charge in the line sensor becomes shorter, and in the case where the sensitivity of the line sensor is low, an S/N ratio decreases. For this reason, a time delay and integration (TDI) sensor has been used, in which a plurality of (stages of) line sensors are arranged in parallel in the transportation direction and charge accumulated in one line sensor is transferred to an adjacent subsequent line sensor. In the TDI sensor, the charge accumulated in a line sensor of the first stage is transferred to a line sensor of the second stage. In a line sensor of the second stage, the charge transferred from the line sensor of the first stage is added to the charge accumulated when the line sensor of the second stage receives light, and the resultant charge is transferred to a line sensor of the third stage. Thus, charge transferred from a line sensor of the previous stage is added sequentially to each line sensor, and accumulated charge transferred to a line sensor of the last stage is output.

Accordingly, in the TDI sensor, in the case where the number of stages is T, charge which is T times as large as that of a single line sensor is accumulated, and a contrast becomes T times as high as that of a single line sensor. Further, noise is reduced, measurement can be performed at high speed, and an S/N ratio increases.

On the other hand, for example, an electrode of a lithium ion battery is produced continuously by unrolling a roll-shaped collector metal foil and applying an electrode material to the foil. Therefore, when a foreign matter in the strip-shaped electrode is detected by X-ray transmission imaging, the electrode is transported continuously to a position between an X-ray source and a sensor by transportation rollers, to thereby detect the foreign matter (Japanese Patent Application Laid-open No. 2004-614793 (FIG. 4)).

By the way, as described above, the TDI sensor has sensitivity higher than that of the line sensor. However, when a distance between a sample and a multi-stage TDI sensor until the sample passes along the TDI sensor changes by a predetermined amount, a feed speed of the sample differs significantly from a feed speed of a transmission image on the TDI sensor to cause displacement of a detection position, with the result that points to be detected are scattered. In this case, there is a problem in that charge is not accumulated conveniently, and an accumulated image is blurred to increase a minimum detectable size, resulting in remarkable degradation in detection accuracy.

In particular, in the case of measuring a transmission X-ray with the TDI sensor while transporting a band-shaped continuous sample as in the electrode of the lithium ion battery with transportation rollers, the sample may be transported to the TDI sensor in a fluttered state. Thus, the above-mentioned problem becomes remarkable.

SUMMARY OF THE INVENTION

The present invention has been made so as to solve the above-mentioned problem, and therefore provides a transmission X-ray analyzer in which a distance between a TDI sensor and a sample transported continuously in a band shape by transportation rollers is kept constant to enhance detection accuracy.

In order to solve the above-mentioned problem, according to an exemplary embodiment of the present invention, there is provided a transmission X-ray analyzer for detecting a transmission X-ray image of a sample that is continuous in a band shape and moves in a predetermined transportation direction, the transmission X-ray analyzer including: a time delay and integration (TDI) sensor including a plurality of two-dimensionally arranged image pickup devices for reading charge generated when an image derived from the transmission X-ray image is subjected to photoelectric conversion, the TDI sensor including a plurality of stages of line sensors including the plurality of two-dimensionally arranged image pickup devices arranged in a direction perpendicular to the predetermined transportation direction, the plurality of stages of line sensors being arranged in the predetermined transportation direction, the TDI sensor being configured to transfer charge accumulated in one line sensor to an adjacent subsequent line sensor; an X-ray source arranged so as to be opposed to the TDI sensor; a pair of support rollers arranged away from the TDI sensor in a detection direction connecting the TDI sensor to the X-ray source between the TDI sensor and the X-ray source, the pair of support rollers being configured to transport the sample to a detection position of the TDI sensor while keeping a constant interval between the TDI sensor and the sample; and a pair of outside rollers arranged respectively on an outer side of the pair of support rollers in the predetermined transportation direction, the pair of outside rollers being configured to transport the sample. One of the pair of support rollers and one of the pair of outside rollers, which are adjacent to each other, are arranged at different positions in the detection direction so as to apply a tension to the sample between the pair of support rollers.

According to the transmission X-ray analyzer, the sample passes along the TDI sensor while being subjected to a tension by the support rollers. Therefore, the sample is not transported to the TDI sensor in a fluttered state, and the distance in the detection direction between the sample and the TDI sensor is kept constant, with the result that detection accuracy can be enhanced while keeping a minute detectable minimum size.

The pair of support rollers may be fixed to the TDI sensor.

Accordingly, the distance in the detection direction between the support rollers and the TDI sensor can be kept with high accuracy.

According to the present invention, the sample is not transported to the TDI sensor in a fluttered state, and the distance in the detection direction between the sample and the TDI sensor can be kept constant, with the result that the detection accuracy of a transmission X-ray can be enhanced while keeping a minute detectable minimum size.

DETAILED DESCRIPTION OF THE PREFERRED EMBODIMENT

Hereinafter, an embodiment of the present invention is described with reference to the drawings.

Figure 1:
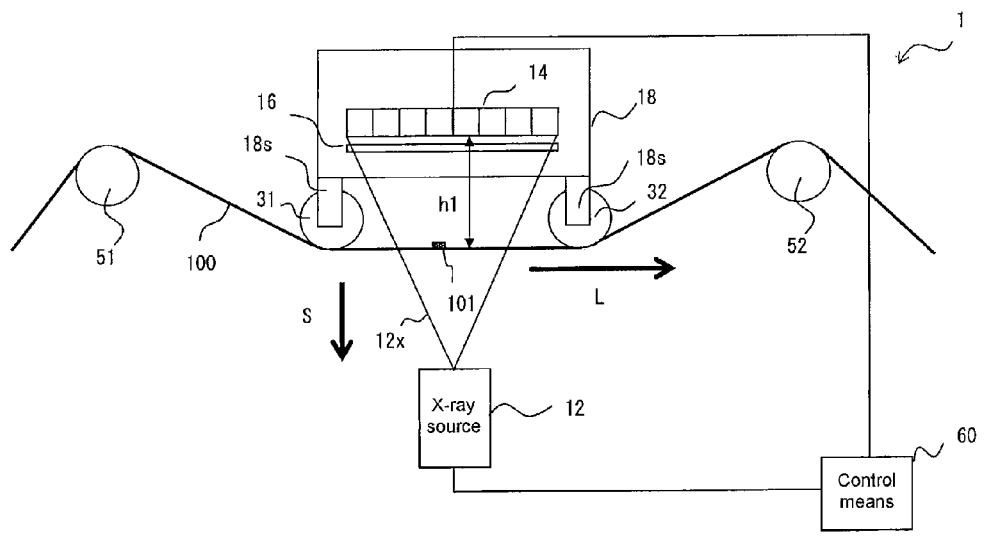
FIG. 1 is a block diagram illustrating a configuration of a transmission X-ray analyzer according to an embodiment of the present invention.

FIG. 1 is a block diagram illustrating a configuration of a transmission X-ray analyzer 1 according to the embodiment of the present invention.

The transmission X-ray analyzer 1 includes an X-ray source 12, a time delay and integration (TDI) sensor 14, a fluorescent screen 16 arranged between the TDI sensor 14 and a sample 100, for converting a transmission X-ray 12x from the sample 100 into fluorescent light (visible light image), a housing 18 for accommodating the TDI sensor 14 and the fluorescent screen 16, a pair of support portions 18s respectively extending downward from both side ends of the housing 18 toward the X-ray source 12, a pair of support rollers 31, 32 pivotally supported by the respective support portions 18s, a pair of outside rollers 51, 52 for transporting the sample 100, and control means 60.

The sample 100 has a sheet shape or a strip shape continuous in the form of a band and is designed to move in a transportation direction L (from left to right in FIG. 1) by the support rollers 31, 32 and the outside rollers 51, 52. The sample 100 is, for example, a lithium cobaltate electrode plate to be used for a positive electrode of a lithium ion battery.

Herein, the X-ray source 12 is arranged below the sample 100. An X-ray is emitted upward from the X-ray source 12 to pass through the sample 100 and is then converted into a visible light image through the fluorescent screen 16. Then, the visible light image is received by the TDI sensor 14 arranged above the sample 100. An X-ray is constantly emitted from the X-ray source 12 so as to continuously analyze the moving sample 100 using the X-ray.

The control means 60 is implemented by a computer, which includes a CPU, a ROM, a RAM, and the like. The control means 60 is capable of executing predetermined computer programs, and performs the overall processing such as the irradiation of X-rays from the X-ray source 12, reception of light of a visible light image by the TDI sensor 14, and output processing.

Further, the transmission X-ray analyzer 1 is configured to detect a foreign matter 101 (e.g., Fe) in the sample 100.

The X-ray source 12 includes a predetermined X-ray tubular bulb. The X-ray tubular bulb, for example, emits as a primary X-ray an X-ray, which is generated by the fact that thermoelectrons generated from a filament (positive electrode) of the tubular bulb are accelerated by a voltage applied between the filament (positive electrode) and a target (negative electrode) to thereby smash against the target (tungsten (W), molybdenum (Mo), chromium (Cr), or the like), from a window of a beryllium foil or the like.

Figure 2A:
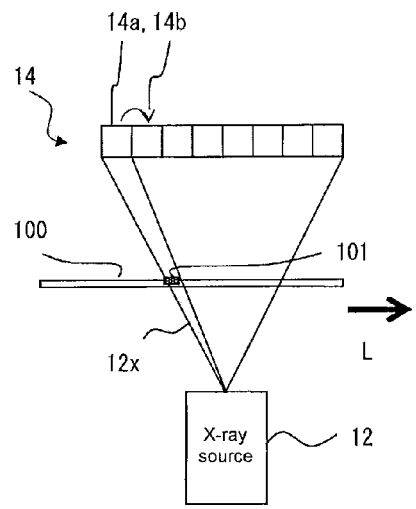
FIGS. 2A and 2B are diagrams illustrating an example of a method of time delay and integration processing through use of a TDI sensor.
Figure 2B:
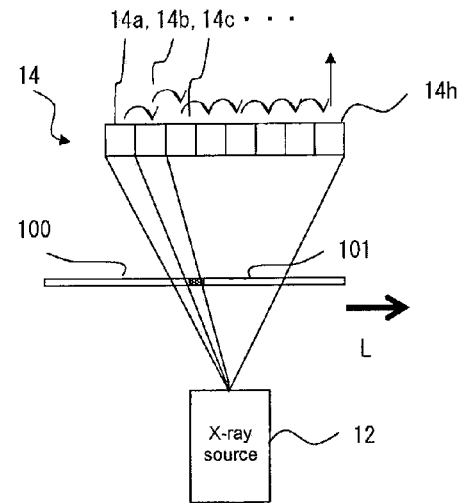

The TDI sensor 14 has a configuration in which a plurality of image pickup devices (charge coupled devices (CCDs)) are arranged in a two-dimensional array. As illustrated in FIGS. 2A and 2B, the TDI sensor 14 has a configuration in which a plurality of stages (eight stages in the example of FIGS. 2A and 2B; however, actually, several hundred to several thousand stages) of line sensors 14a to 14h having image pickup devices arranged in a direction perpendicular to the transportation direction L are arranged in the transportation direction L.

The respective rollers 31, 32, 51, and 52, which are features of the present invention, are hereinafter described. The support rollers 31, 32 pivotally supported by the respective support portions 18s can respectively rotate about an axis in a direction perpendicular to the drawing sheet. Further, the support rollers 31, 32 are arranged away from the TDI sensor 14 in a detection direction S (vertical direction in FIG. 1) connecting the TDI sensor 14 to the X-ray source 12, and the sample 100 is transported to a detection position of the TDI sensor 14 while coming into contact with the lower surfaces of the support rollers 31, 32. In this case, the TDI sensor 14 and the lower surfaces of the support rollers 31, 32 are away from each other by a distance h1 in the detection direction S, and hence, an interval between the TDI sensor 14 and the sample 100 is also kept at the predetermined distance h1.

On the other hand, the outside rollers 51, 52 are arranged respectively on an outer side of the support rollers 31, 32 in the transportation direction L. Further, in the detection direction S, the support roller 31 and the outside roller 51 adjacent to each other (and the support roller 32 and the outside roller 52 adjacent to each other) are arranged at different positions. For example, in the example of FIG. 1, the outside roller 51 is positioned higher than the support roller 31, and the outside roller 52 is also positioned higher than the support roller 32. Then, the sample 100 is transported while coming into contact with the upper surfaces of the respective outside rollers 51, 52. Thus, the pair of support rollers 31, 32 holds the sample 100 passing along the respective outside rollers 51, 52 so as to push down the sample 100, and thereby, can apply a tension to the sample 100 between the pair of support rollers 31, 32.

As described above, the sample 100 passes along the multi-stage TDI sensor 14 while being subjected to a tension by the support rollers 31, 32. Therefore, the sample 100 is not transported to the TDI sensor 14 in a fluttered state, and a distance in the detection direction S between the sample 100 and the TDI sensor 14 is kept constant, with the result that detection accuracy can be enhanced while keeping a minute detectable minimum size.

Further, in this embodiment, the support rollers 31, 32 are fixed to the TDI sensor 14 (to the housing 18 of the TDI sensor 14). Therefore, a distance in the detection direction S between the support rollers 31, 32 and the TDI sensor 14 can be kept with high accuracy.

In addition to the above-mentioned sample, examples of the sample 100 include, but are not limited to, a graphitecoated electrode plate to be used as a negative electrode of a lithium ion battery, a separator of a battery, an ion-exchange membrane for a fuel cell, and an insulating film for a multi-layer circuit board. Further, a length of the sample 100 can be set to about 500 to 1,000 m and a transportation speed thereof can be set to about 10 to 100 m/min, although not limited thereto. As the support rollers 31, 32, for example, support rollers which have a width of about 60 to 1,000 mm can be used, although not limited thereto.

A tension applied to the sample 100 between the support rollers 31, 32 can be set to about 5 to 10 N/cm in the case of an electrode plate for a lithium ion battery.

Next, an example of a method of time delay and integration processing through use of the TDI sensor 14 is described with reference to FIGS. 2A and 2B. Herein, the TDI sensor 14 includes the plurality of stages (eight stages) of line sensors 14a to 14h.

Assuming that the foreign matter 101 in the sample 100 enters a light-receiving region of the line sensor 14a of the first stage, charge accumulated in the line sensor 14a is transferred to the line sensor 14b of the second stage (FIG. 2A). Next, assuming that the foreign matter 101 moves in the transportation direction L and enters a light-receiving region of the line sensor 14b of the second stage, charge is accumulated in the line sensor 14b (FIG. 2B).

In the line sensor 14b of the second stage, the charge transferred from the line sensor 14a of the first stage is added to the charge accumulated when the line sensor 14b of the second stage receives light, and the resultant accumulated charge is transferred to the line sensor 14c of the third stage. Thus, charge transferred from a line sensor of the previous stage is added sequentially to each of the line sensors 14a to 14h, and accumulated charge transferred to the line sensor 14h of the last stage is output. Then, the sample 100 moving in the transportation direction L is subjected to a line analysis continuously, with the result that two-dimensional image data of the sample 100 is obtained continuously.

Accordingly, in the TDI sensor 14, in the case where the number of stages is T, charge which is T times as large as that of a single line sensor is accumulated, and a contrast becomes T times as high as that of a single line sensor. Further, noise is reduced, measurement can be performed at high speed, and an S/N ratio increases.

Note that, as the configuration and operation of the TDI sensor 14, publicly-known configuration and operation can be used.

Figure 3:
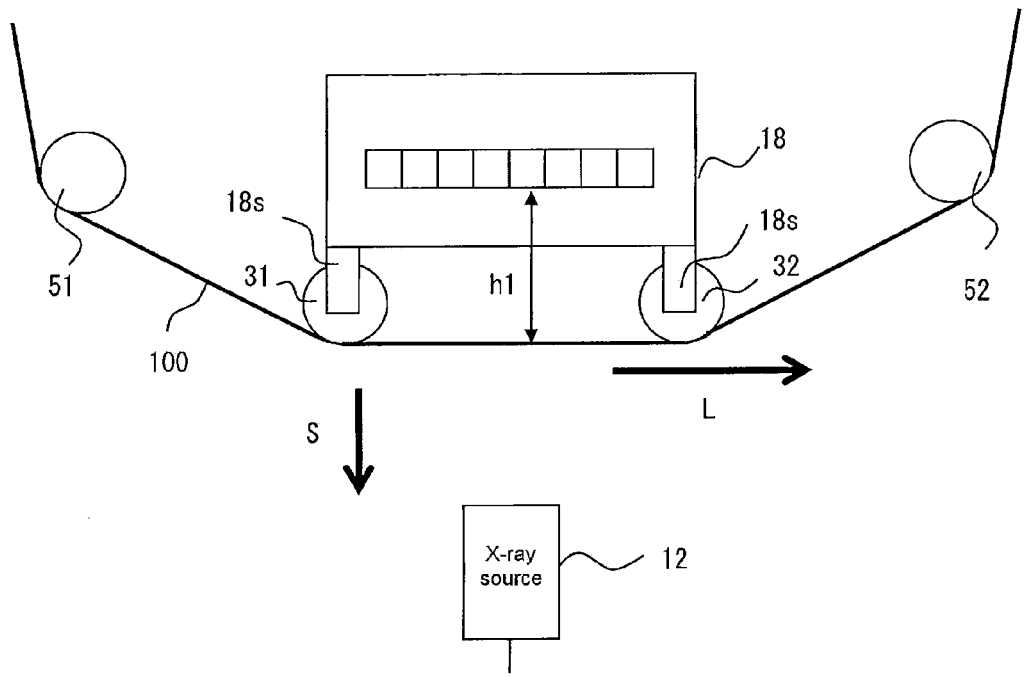
FIG. 3 is a diagram illustrating a modified example in which the position of a sample passing along each roller is changed.

FIG. 3 illustrates a modified example in which the position of the sample 100 passing along the respective rollers 31, 32, 51, and 52 is changed. In FIG. 3, the outside roller 51 is positioned higher than the support roller 31, and the outside roller 52 is also positioned higher than the support roller 32 in the same way as in FIG. 1. On the other hand, the sample 100 is transported while coming into contact with the lower surfaces of the respective outside rollers 51, 52 and support rollers 31, 32. Thus, the sample 100 is placed at a lowest point at the positions of the pair of support rollers 31, 32, and can be subjected to a tension between the pair of support rollers 31, 32.

Figure 4:
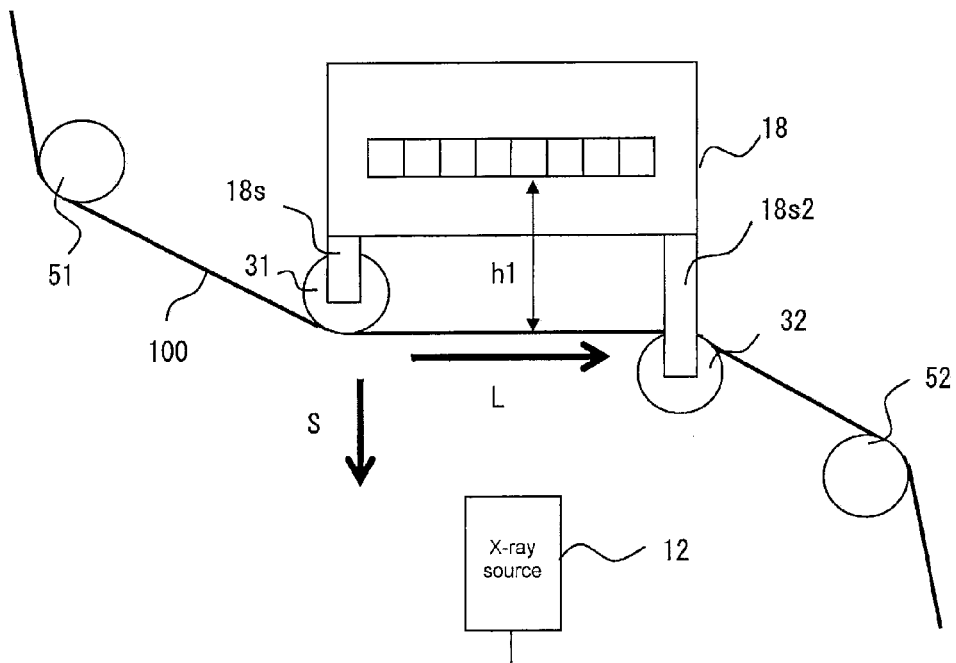
FIG. 4 is a diagram illustrating a modified example in which the arrangement state of each roller and the position of a sample passing along each roller are changed.

FIG. 4 illustrates a modified example in which the arrangement state of the respective rollers 31, 32, 51, and 52 and the position of the sample 100 passing along the respective rollers 31, 32, 51, and 52 are changed. In FIG. 4, a length of a support portion 18s2 on the right side is set to be larger than that of the support portion 18s on the left side, and a distance between the TDI sensor 14 and the lower surface of the support roller 31 is set to be equal (distance h1) to that between the TDI sensor 14 and the upper surface of the support roller 32 in the detection direction S. Then, the sample 100 is transported to the TDI sensor 14 while coming into contact with the lower surface of the support roller 31 and is output from the TDI sensor 14 while coming into contact with the upper surface of the support roller 32. Accordingly, an interval between the TDI sensor 14 and the sample 100 can also be kept at the predetermined distance h1.

On the other hand, the outside roller 51 is positioned higher than the support roller 31, and the outside roller 52 is positioned lower than the support roller 32. Then, the sample 100 is transported while coming into contact with the lower surface of the outside roller 51 and the upper surface of the outside roller 52. Even in the example of FIG. 4, the sample 100 can be subjected to a tension between the pair of support rollers 31, 32.

Figure 5:
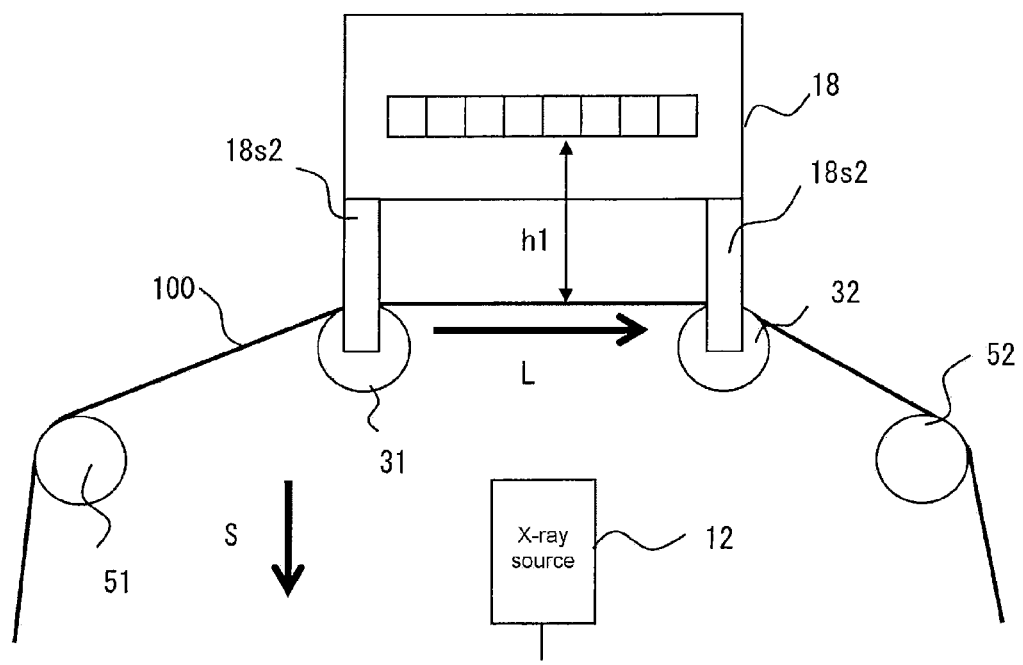
FIG. 5 is a diagram illustrating another modified example in which the arrangement state of each roller and the position of a sample passing along each roller are changed.

FIG. 5 illustrates another modified example in which the arrangement state of the respective rollers 31, 32, 51, and 52 and the position of the sample 100 passing along the respective rollers 31, 32, 51, and 52 are changed. In FIG. 5, lengths of both the support portions 18s2 are set to be larger than those of the support portions 18s of FIG. 1, and a distance between the TDI sensor 14 and the lower surface of the support roller 31 is set to be equal (distance h1) to that between the TDI sensor 14 and the lower surface of the support roller 32 in the detection direction S. Then, the sample 100 is transported to the TDI sensor 14 while coming into contact with the upper surfaces of the support rollers 31, 32. Accordingly, an interval between the TDI sensor 14 and the sample 100 can also be kept at the predetermined distance h1.

On the other hand, the outside roller 51 is positioned lower than the support roller 31, and the outside roller 52 is positioned lower than the support roller 32. Then, the sample 100 is transported while coming into contact with the upper surfaces of the outside rollers 51, 52. Even in the example of FIG. 5, the sample 100 can be subjected to a tension between the pair of support rollers 31, 32.

It is to be understood that the present invention is not limited to the embodiment described above, and that the scope of the present invention encompasses various modifications and equivalents included in the idea and the scope of the present invention.

For example, the arrangement state of the support rollers and the outside rollers, and the position of the sample passing along the respective rollers are not limited to the examples of FIGS. 1 and 3 to 5 described above. The adjacent support roller and outside roller only need to be arranged at different positions in the detection direction so that a tension can be applied to the sample between the pair of support rollers.

Further, the support roller and the outside roller may be driving rollers or rollers that merely spin.

Further, the support roller is not required to be fixed to the TDI sensor (to the housing of the TDI sensor), and may be pivotally supported by a support portion separate from the TDI sensor.

What is claimed is:

1. A transmission X-ray analyzer for detecting a transmission X-ray image of a sample that is continuous in a band shape and moves in a predetermined transportation direction, the transmission X-ray analyzer comprising:
   a time delay and integration (TDI) sensor comprising a plurality of two-dimensionally arranged image pickup devices for reading charge generated when an image derived from the transmission X-ray image is subjected to photoelectric conversion,
      the TDI sensor comprising a plurality of stages of line sensors including the plurality of two-dimensionally arranged image pickup devices arranged in a direction perpendicular to the predetermined transportation direction, the plurality of stages of line sensors being arranged in the predetermined transportation direction, the TDI sensor being configured to transfer charge accumulated in one line sensor to an adjacent subsequent line sensor;

an X-ray source arranged so as to be opposed to the TDI sensor;

a pair of support rollers arranged away from the TDI sensor in a detection direction connecting the TDI sensor to the X-ray source between the TDI sensor and the X-ray source, the pair of support rollers being configured to transport the sample to a detection position of the TDI sensor while keeping a constant interval between the TDI sensor and the sample; and a pair of outside rollers arranged respectively on an outer side of the pair of support rollers in the predetermined transportation direction, the pair of outside rollers being configured to transport the sample, wherein one of the pair of support rollers and one of the pair of outside rollers, which are adjacent to each other, are arranged at different positions in the detection direction so as to apply a tension to the sample between the pair of support rollers.

2. A transmission X-ray analyzer according to claim 1, wherein the pair of support rollers is fixed to the TDI sensor.

\* \* \* \* \*